United States Patent [19]

Clarke

[11] 4,145,429

[45] Mar. 20, 1979

[54] ORAL VETERINARY PREPARATIONS

[75] Inventor: Christopher D. Clarke, Worthing, England

[73] Assignee: Beecham Group Limited, Great Britain

[21] Appl. No.: 776,495

[22] Filed: Mar. 11, 1977

Related U.S. Application Data

[63] Continuation of Ser. No. 611,005, Sep. 8, 1975, abandoned.

[30] Foreign Application Priority Data

Sep. 21, 1974 [GB] United Kingdom ............... 41231/74

[51] Int. Cl.$^2$ ..................... A61K 31/43; A61K 31/14; A61K 47/00

[52] U.S. Cl. .................................. 424/271; 424/329; 424/357; 424/358

[58] Field of Search ........................ 424/357, 329, 271

[56] References Cited

U.S. PATENT DOCUMENTS

2,914,443  11/1959  Lynch .................................. 424/357

*Primary Examiner*—Sam Rosen
*Attorney, Agent, or Firm*—Jacobs & Jacobs

[57] ABSTRACT

A fluid pharmaceutical formulation for oral administration to animals comprising a medicament, an edible oil and an oleophilic clay. The oleophilic clay thickening agent is formed by replacement of inorganic cations in a natural or synthetic clay or organic cations.

11 Claims, No Drawings

ORAL VETERINARY PREPARATIONS

This is a continuation, of Ser. No. 611,005 filed Sept. 8, 1975, now abandoned.

This invention relates to pharmaceutical formulations and in particular to oil-based formulations for oral administration of medicaments to domestic animals.

For the administration of insoluble medicaments to animals by the oral route, the medicament is often presented as a suspension. In preparing such a suspension, it is generally desirable that the formulation base is of such a viscosity that the suspended material does not readily sediment out. For reasons of stability, ready-to-use antibiotic suspensions are customarily prepared in an oily base. In order to produce an oily base which is sufficiently gel-like, the oil is heated in the presence of a suitable thickening agent, typically aluminium stearate. Such a process is lengthy and involved and therefore expensive. In addition, the rheological characteristics of the final gel are markedly influenced by slight variations in the time/temperature conditions obtained during manufacture.

It is therefore an object of the present invention to provide an oil-based formulation which is simple and economical to prepare commercially, shows minimum batch to batch variation, and is sufficiently gel-like to be suitable as a base for the incorporation of medicaments, and their oral administration to animals.

Accordingly, the present invention provides a fluid pharmaceutical formulation for oral administration to animals which formulation comprises a medicament, an edible oil and an oleophilic clay.

By the term oleophilic clay used herein is meant a natural or synthetic clay which has been rendered more easily dispersable in edible oil by replacement of inorganic cations therein by organic cations.

Suitable organic cations include ammonium ions substituted by at least one $C_{12-18}$ alkyl group. Examples of such cations include cations of the formula (I):

where $R_1$ is a $C_{12-18}$ alkyl group, $R_2$ is either a second $C_{12-18}$ alkyl group, a benzyl group, a $C_{1-6}$ alkyl group or hydrogen, and $R_3$ and $R_4$ are each a $C_{1-6}$ alkyl group or hydrogen. Examples of suitable cations within formula (I) include octadecyl ammonium, dimethyl mono- and di-octadecyl ammonium, dimethyl hexadecyl ammonium, and dimethyl benzyl octadecyl ammonium ions. Preferably in formula (I) $R_1$ is a $C_{15-18}$ alkyl group, $R_2$ is a $C_{15-18}$ alkyl group or a benzyl, methyl or ethyl group or hydrogen, and $R_3$ and $R_4$ are each a methyl or ethyl group or hydrogen.

Suitable clays for this ion-exchange treatment and subsequent use in the invention are usually those characterised by a high cation exchange capacity and high surface area.

Examples of oleophilic clays include those clays sold commercially as Bentones (modified Bentonite, Berk Ltd.) and Attagels (modified Attapulgite, Engelhard). The Bentones are montmorillonites in which inorganic cations have been replaced by alkyl ammonium cations as described above, normally octadecyl ammonium, dimethyl mono- or di-octadecyl ammonium, dimethyl hexadecyl or dimethyl benzyl octadecyl ammonium ions, or similarly substituted hectorites. The Attagels are similarly substituted hydrated magnesium aluminium silicates belonging to the montmorillonite group of clays, but having a higher magnesium content than normal montmorillonites and containing traces of calcium and iron.

Oleophilic clays have been reported as additives for ointment bases (Billups and Seger, Am. J. Pharm., 1964, 136, 183–205) but such topical formulations are not of course sufficiently fluid for ready oral administration forms and there is no suggestion in that publication of fluid oil-based formulations containing the modified clays, or of their advantageous properties.

The edible oil employed in the formulations of this invention should not be liable to substantial drying or oxidation. Preferably a vegetable oil is employed and suitable examples include sunflower oil, arachis oil, soya-bean oil, rapeseed oil, and maize oil.

The present formulations are of value for any type of medicament and are particularly useful for orally administrable antibiotics, such as ampicillin, amoxycillin, cloxacillin, flucloxacillin, and the 5-indanyl and phenyl esters of carbenicillin, and other antibiotics useful in the treatment of gut infections. Such medicaments usually represent 1 to 15% of the formulation, suitably 3 to 10% of the formulation.

A polar solvent may also be advantageously incorporated into the formulations in order to increase the ease with which the oleophilic clays may be fully dispersed in the edible oil during the preparation of the formulation. It is necessary that the solvent be compatible with the medicament, non-toxic, substantially more polar than the edible oil and miscible with the edible oil. For penicillins, a suitable polar solvent is propylene carbonate. The polar solvent may constitute from 0 to 2% of the total formulation and in general the polar solvent will be present in the formulation in a weight that is 0 to 40% of the weight of oleophilic clay.

The amount of oleophilic clay present in the formulation to produce the desired properties will normally be in the range of 0.1 to 25%. Obviously lower percentage inclusions will be preferred when a polar solvent is present, higher percentage inclusions preferred in the absence of a polar solvent. In general however 1 to 5% of oleophilic clay will normally be most satisfactory, preferably in the presence of 0.1 to 2.0% of polar solvent.

When the formulation is to be used for the treatment of an animal diarrhoea or scours, it may also be of advantage to include in the formulation a natural or synthetic clay absorbent. The amount of such clay present may be from 1 to 20%, preferably 5 to 15%, and examples of such clays include Bentonite and Attapulgite.

The edible oil will represent the balance of the formulation, and will normally be present as at least 50%, suitably as at least 75%, of the formulation.

From the foregoing, it can be seen that a prefered embodiment of this invention is a pharmaceutical formulation as defined above which comprises 1 to 15% medicament, 1 to 5% oleophilic clay, 0.1 to 2.0% polar solvent, and edible oil to 100%. Into this prefered formulation may suitably be incorporated 5 to 15% of natural or synthetic clay absorbent.

In a further aspect, this invention provides a process for the preparation of a fluid pharmaceutical formulation which process comprises mixing a medicament with a dispersion of an oleophilic clay in an edible oil.

If a polar solvent is to be used, it is normal to add the solvent to the dispersion of the clay in the oil before the mixing step with the medicament is carried out. Also, if a natural or synthetic clay absorbent is to be used, it is normally mixed into the dispersion of the clay in oil at the same time as the medicament.

The clay in oil dispersion, optionally containing the polar solvent, is preferably passed through a colloid mill before it is mixed with the medicament and optional natural or synthetic clay absorbent. Similarly the final suspension is preferably passed through a colloid mill before use.

The invention also provides a method of preventing or treating a disease in domestic animals, which method comprises the oral administration of a fluid pharmaceutical formulation as hereinbefore defined. The formulation is normally administered by means of a suitable dispenser, such as a nozzle connected to a bottle and plunger. A single dose may be for example 1 to 10 mls. of the suspension, containing a concentration of medicament which is in accordance with the recommended dosage of that medicament.

The formulation of the invention containing an appropriate medicament is of particular use in the treatment of animal diarrhoea or scours, and in particular in the treatment of neonatal scours in piglets.

The following Examples illustrate the invention:

EXAMPLE 1

The following formulation was prepared by the method set out below:

| Bentone 38 (1) | 1.5% | w/v |
| --- | --- | --- |
| Propylene Carbonate | 0.6% | w/v |
| Pharmasorb (2) | 10% | w/v |
| Phosphoric Acid (3) | 0.1% | w/v |
| Ampicillin Trihydrate | 6.0% | w/v as free acid |
| Soya-bean Oil | to 100% | |

(1) Bentone 38 is dimethyl dioctadecyl ammonium hectorite, $[Mg_8LiSi_{12}O_{30}(OH)_6]^{\ominus}[(CH_3)_2N(C_{18}H_{37})_2]^{\oplus}$
(2) Pharmasorb is a brand of activated Attapulgite, Attapulgite having the approximate composition as defined earlier in the specification.
(3) The phosphoric acid is present in a minor proportion to balance the alkaline pH of the Bentone.

The Bentone was dispersed in the soya-bean oil, and when thoroughly distributed, the propylene carbonate was added with high speed mixing, followed by colloid milling to produce the base. Into this base was first mixed the phosphoric acid, and then the pharmasorb and the penicillin, and the resultant suspension was then passed through a colloid mill once more.

EXAMPLE 2

Example 1 was repeated, but using amoxycillin trihydrate in place of the ampicillin trihydrate.

EXAMPLE 3

The following formulation was prepared by the method of Example 1:

| Bentone 27 (1) | 1.75% | w/v |
| --- | --- | --- |
| Propylene Carbonate | 0.6% | w/v |
| Pharmasorb | 10.0% | w/v |
| Ampicillin Trihydrate | 5.0% | w/v |
| Sunflower Oil | to 100% | |

(1) Bentone 27 is dimethyl benzyl octadecyl ammonium hectorite, $[Mg_8LiSi_{12}O_{30}(OH)_6]^{\ominus}[(CH_3)_2N(C_{18}H_{37})(CH_2C_6H_5)]^{\oplus}$

EXAMPLE 4

Example 3 was repeated, but using amoxycillin trihydrate in place of the ampicillin trihydrate.

What we claim is:
1. In the treatment of a veterinary animal with an orally effective antibiotic, the improvement which comprises orally administering said antibiotic in veterinary fluid composition consisting essentially of from 1 to 15% w/v of an antibiotic, from 1 to 5% w/v of a natural or synthetic clay in which inorganic cations have been replaced with long chain aliphatic quaternary ammonium cations, from 0 to 2% w/v of a polar solvent and, as the balance, an edible vegetable oil.
2. The method according to claim 1 wherein said long chain aliphatic ammonium cations are of the formula:

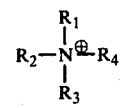

wherein $R_1$ is alkyl of 12 to 18 carbon atoms, $R_2$ is hydrogen, alkyl of 1 to 6 carbon atoms, benzyl or alkyl of 12 to 18 carbon atoms, and each of $R_3$ and $R_4$ are hydrogen or alkyl of 1 to 6 carbon atoms.
3. The method according to claim 2 wherein said cations are octadecylammonium, dimethyl mono- or di-octadecylammonium, dimethylhexadecylammonium or dimethylbenzyloctadecylammonium cations.
4. The method according to claim 1 wherein said clay is of the montmorillonite group.
5. The method according to claim 1 wherein said edible vegetable oil is sunflower oil, arachis oil, soyabean oil, rapeseed oil or maize oil.
6. The method according to claim 1 wherein said antibiotic is a penicillin.
7. The method according to claim 6 wherein said penicillin is cloxacillin, flucloxacillin, the 5-indanyl or phenyl ester of carbenicillin, ampicillin or amoxycillin.
8. The method according to claim 1 wherein said composition contains in addition a natural or synthetic clay absorbent.
9. The method according to claim 6 wherein said penicillin is ampicillin.
10. A method according to claim 1 wherein the composition is orally administered in the treatment of neonatal scours in piglets.
11. In the treatment of a veterinary animal with an orally effective penicillin, the improvement which comprises orally administering veterinary fluid composition consisting essentially of from 1 to 15% w/v of said penicillin, from 1 to 5% w/v of a clay of the montmorillonite group in which organic cations have been replaced by a quaternary ammonium cation of the formula:

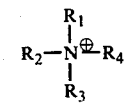

from about 0 to 2% of a polar solvent and, as the balance, an edible vegetable oil selected from the group consisting of sunflower oil, arachis oil, soyabean oil, rapeseed oil or maize oil.

* * * * *